United States Patent [19]

Leiner

[11] Patent Number: 5,658,451
[45] Date of Patent: Aug. 19, 1997

[54] METHOD FOR CALIBRATION OF A PH MEASURING ELEMENT

[75] Inventor: Marco Jean-Pierre Leiner, Graz, Austria

[73] Assignee: AVL Medical Instruments AG, Schaffhausen, Switzerland

[21] Appl. No.: 563,277

[22] Filed: Nov. 28, 1995

[30] Foreign Application Priority Data

Feb. 1, 1995 [AT] Austria .................. 173/95

[51] Int. Cl.$^6$ .................. G01N 27/26; G01N 27/136
[52] U.S. Cl. .................. 205/787.5; 204/400; 204/416; 204/418; 204/419; 204/420; 205/775; 205/792; 436/8; 436/9; 436/11
[58] Field of Search .................. 204/400, 401, 204/403, 416, 418, 419, 420; 205/775, 787.5, 792; 436/8, 9, 11, 19

[56] References Cited

U.S. PATENT DOCUMENTS

| | | | |
|---|---|---|---|
| 3,681,255 | 8/1972 | Wilfore | 205/87.5 |
| 3,912,614 | 10/1975 | Spracklen et al. | 204/415 |
| 5,080,865 | 1/1992 | Leiner et al. | |
| 5,204,265 | 4/1993 | Nelson et al. | 204/403 |
| 5,228,350 | 7/1993 | Karpf et al. | |
| 5,325,853 | 7/1994 | Morris et al. | 204/403 |
| 5,351,563 | 10/1994 | Karpf et al. | |

FOREIGN PATENT DOCUMENTS

| | | |
|---|---|---|
| 392364 | 3/1991 | Austria . |
| 0354895 | 2/1990 | European Pat. Off. . |
| 0460343 | 12/1991 | European Pat. Off. . |

*Primary Examiner*—T. Tung
*Attorney, Agent, or Firm*—Watson Cole Stevens Davis, P.L.L.C.

[57] ABSTRACT

In a method for calibration of a pH measuring element whose ion-permeable, hydrophilic polymer layer is brought into contact with an aqueous solution prior to calibration, the aqueous solution is displaced or replaced by a gaseous calibrating medium, and residues of the aqueous solution remaining in the ion-permeable polymer layer. The gaseous calibrating medium contains a known amount of at least one component which is acid or basic in aqueous solution which reacts with the remaining residues of the aqueous solution in the polymer layer, such that a defined pH value is established in the polymer layer, which is employed for calibration of the measuring element.

14 Claims, 2 Drawing Sheets

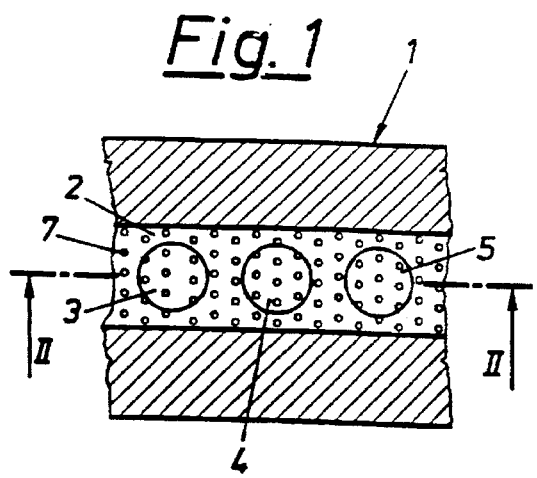
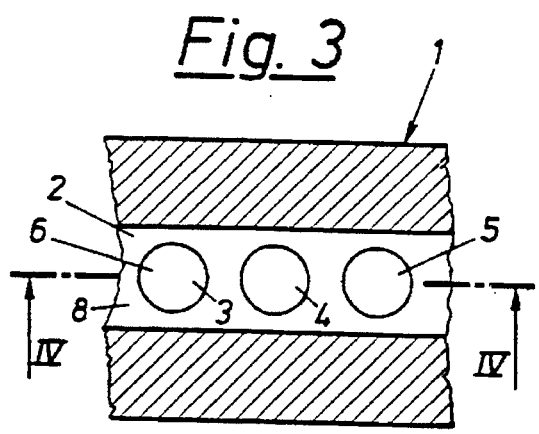
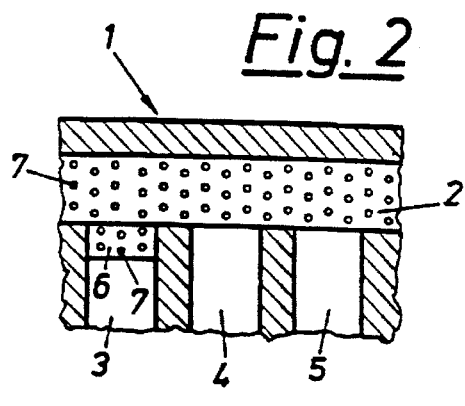
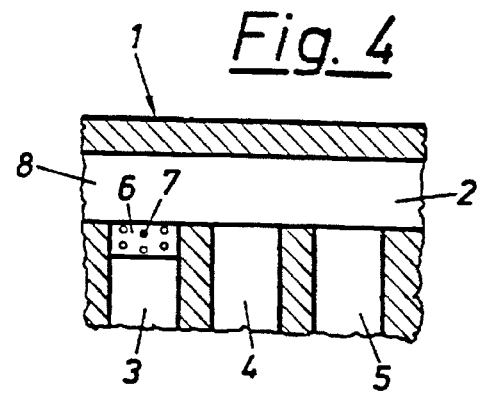
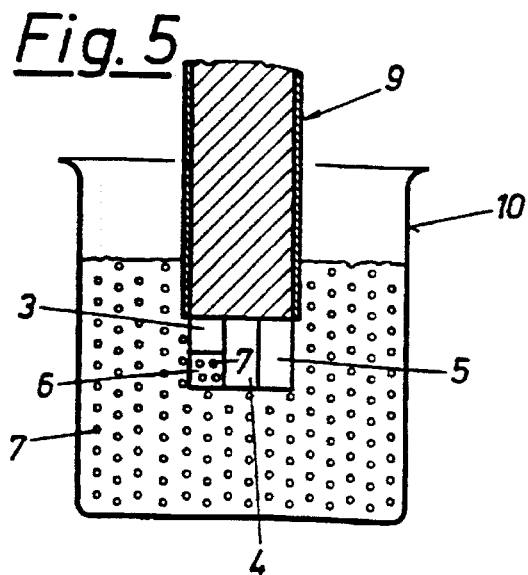
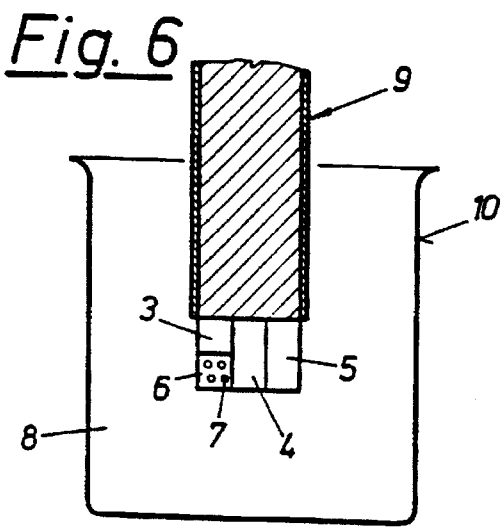

METHOD FOR CALIBRATION OF A PH MEASURING ELEMENT

BACKGROUND OF THE INVENTION

This invention relates to a method for calibration of a pH measuring element whose ion-permeable, hydrophilic polymer layer is brought into contact with an aqueous solution prior to calibration.

DESCRIPTION OF THE PRIOR ART

Especially in blood gas analysis it is essential that pH, $PO_2$, and $PCO_2$ parameters be determined simultaneously. For this reason various measuring devices for continuous (invasive) and discontinuous measurement of these parameters have been developed. Measuring usually takes place in a single process with the use of three different electrochemical measuring elements (Ole Siggaard-Andersen, The Acid-Base Status of the Blood, Munksgaard, Copenhagen 1974, 4th edition) or optical measuring elements (European Patent Application No. 0 354 895) integrated into a measuring device.

Before calibration takes place, the measuring element is conveniently kept in contact with an aqueous medium.

To calibrate the measuring elements, the measuring process must be preceded by a calibrating step in which each measuring element is brought into contact with at least one calibrating medium with known values for the substance to be measured.

Suitable calibrating media for optical and electrochemical pH measuring elements are buffer solutions containing the quantity to be determined in known and stable concentration. In order to calibrate a pH measuring element, it is usually necessary that the pH measuring element be brought into contact with at least one calibrating liquid of known pH. From the resulting optical or electrical signals, the characteristic of the measuring element may be obtained.

Calibration of optical and electrochemical $CO_2$ and $O_2$ measuring elements according to European Patent Application No. 0 460 343, for example, is effected with the use of gases or gas mixtures of known $CO_2$ and $O_2$ partial pressures. In blood gas analysis, in particular, suitable calibration points are 50–90 and 140–160 torr $O_2$ for the $O_2$ measuring element, and 35–45 and 75–85 torr $CO_2$ for the $CO_2$ measuring element.

In European Patent Application No. 0 354 895 a steam-saturated gas mixture at atmospheric pressure is proposed as a calibrating and storage medium, which contains 60 to 160, preferably 90 mm Hg $O_2$, and 20 to 60, i.e., preferably 35 mm Hg $CO_2$, and an inert gas, preferably nitrogen. Whereas such a calibrating medium lends itself to the calibration of optical sensors measuring $CO_2$ and $O_2$ concentrations, it does not permit direct calibration of pH sensors, as a defined pH value can only be obtained in aqueous solution, and a steam saturated gas mixture is not suitable for pH calibration unless additional provisions are made.

$CO_2$ measuring elements are frequently calibrated with tonometric liquids (i.e., liquids that have been equilibrated with gases of known composition) or with liquids prepared just before calibration.

Liquid calibrating media which may be used for calibration of $CO_2$ and pH measuring elements, are characterized by a known $CO_2$ concentration or $CO_2$ partial pressure and a known pH value. Austrian Patent No. 392 364, for instance, discloses a method for simultaneous calibration of pH and $CO_2$ measuring elements with the use of liquid calibrating media and for the preparation of such media. The described method utilizes two liquids of good storage stability under normal atmospheric conditions, and a suitable device for mixing the two liquids, which is detached from the measuring chamber.

An $O_2$-free calibrating solution suitable for zero-point calibration of an $O_2$ measuring element may contain a reagent consuming the oxygen by a chemical reaction, for example.

Liquid calibrating media which are suitable for calibration of $O_2$ measuring elements outside of the zero point, must further have a defined $O_2$ concentration (or $O_2$ partial pressure). Due to the low $O_2$ solubility of liquid calibrating media considerable technical expense is involved in the preparation and handling of such media compared with the use of gaseous media.

Due to the use of different liquid and gaseous calibrating media for a number of measuring elements integrated in a measuring device, expenses for preparation of these liquid and gaseous media are considerable. In addition, different media necessitate complex measuring arrangements accompanied by long waiting periods due to complex calibration processes.

Following are comments and examples illustrating the problems that are encountered when optical or electrochemical pH measuring elements are calibrated, in particular, when $O_2$ and $CO_2$ measuring elements are calibrated simultaneously.

Electrochemical pH measuring elements include glass electrodes, liquid membrane electrodes, antimony electrodes, field effect transistors (ISFET), solid-state systems, such as precious metal/precious metal oxide systems (Ir/IrO$_2$, Pd/PdO$_2$), redox systems (quinhydrone electrodes), and polypyrroles.

Optical pH measuring elements mostly contain pH indicators in the form of organic acids or bases, which are supplied in an ion-permeable, hydrophilic polymer layer (for instance, a hydrogel) or directly attached to an optical waveguide. Suitable pH indicators are absorption dyes, luminescence dyes, and polymers (such as polyaniline). These indicators are brought into at least indirect contact with the sample.

In dependence on the pH value (pH=$-\log(aH^+)$) thermodynamic equilibrium is established between the protonated form (acid) and the deprotonated form (conjugate base) of the indicator, in accordance with the reaction equation $$HA \xrightarrow{Ka} A^- + H^+$$

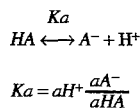

$$Ka = aH^+ \frac{aA^-}{aHA}$$

HA standing for the acid form and $A^-$ for the conjugate base form of the indicator, Ka for the thermodynamic equilibrium constant and a for the activity.

The two chemical forms HA and $A^-$ of the indicator are characterized by different colorimetric and/or luminescent properties. For example, if the absorption or fluorescence intensity of the conjugate base ($A^-$) is used to determine the pH value, the absorption or fluorescence intensity of the basic form ($A^-$) must be determined with the use of at least one calibrating medium of known pH in order to calibrate a measuring element with such an indicator.

Suitable calibrating media for optical and electrochemical pH measuring elements include liquid media (buffers) of a known and stable pH value subject to little or no change when small amounts of acid or basic components are added or when the medium is diluted.

In particular, aqueous liquids containing weak acids and their salts at a 1:1 ratio have marked buffering properties. Buffering capacity increases with an increase in the concentration of the buffer components.

Examples for calculating the pH values of common buffer systems are given in Claus Bliefert, pH-Wert Berechnungen, Verlag Chemie, Weinheim 1987 (Germany). In blood gas analysis pH meters often are calibrated at pH 7.4 and 6.8, approximately.

A first liquid calibrating medium, which is used frequently, is a solution of 0.008695 mole/kg $KH_2PO_4$ and 0.03043 mole/kg $Na_2HPO_4$, for example. At 37° C. and in equilibrium with $CO_2$-containing gases of different $CO_2$ partial pressures, this calibrating solution A has the following pH values,

| $PCO_2$ (torr) | pH |
| --- | --- |
| 0 | 7.38 |
| 40 | 6.97 |
| 80 | 6.83 |

A second liquid calibrating medium is an aqueous solution of 0.025 mole/kg $KH_2PO_4$ and 0.025 mole/kg $Na_2HPO_4$, for example. At 37° C. and in equilibrium with $CO_2$-containing gases of different $CO_2$ partial pressures, this calibrating solution B has the following pH values,

| $PCO_2$ (torr) | pH |
| --- | --- |
| 0 | 6.84 |
| 40 | 6.69 |
| 80 | 6.60 |

For calibration of an optical or electrochemical $CO_2$ measuring element for use in blood gas analysis, it is recommended that at least one calibrating medium be used whose $CO_2$ partial pressure should be in the physiologically normal range of blood (35–45 torr $CO_2$). A second calibrating medium should have a $CO_2$ partial pressure of 80 torr.

The above table shows that the two phosphate buffers frequently employed for calibrating pH measuring elements, are not suitable for simultaneously calibrating the $CO_2$ measuring element, as in equilibrium with 40 torr $CO_2$ no pH value can be obtained in the physiologically normal range (7.35–7.45).

Moreover, equilibration (tonometry) of the liquid calibrating media with gases of known composition will necessitate suitable devices and comparatively large amounts of gas.

For simultaneous calibration of an $O_2$ measuring element provided in the measuring device a liquid calibrating medium is not commendable because of the poor oxygen solubility of aqueous media.

Although gaseous calibrating media could be advantageously used with $CO_2$ and $O_2$ measuring elements, they are not suitable for pH meters and hence do not allow simultaneous calibration of all three measuring elements.

SUMMARY OF THE INVENTION

It is an object of the invention to propose a calibrating method for a pH measuring element, and which is also suited for simultaneous calibration of further measuring elements provided in a measuring device. According to the invention, the method should lend itself to the calibration of both single pH measuring elements and pH measuring elements combined with any other measuring elements for gases (such as $CO_2$, $O_2$, $SO_2$, $NH_3$, $H_2S$, volatile organic compounds).

In the invention this object is achieved by providing that an aqueous solution be displaced or replaced by a gaseous calibrating medium, residues of the aqueous solution remaining in the ion-permeable polymer layer, and that the gaseous calibrating medium contain a known amount of at least one component which is acid or basic in aqueous solution and which reacts with the remaining residues of the aqueous solution in the polymer layer, such that a defined pH value is established in the polymer layer, which is employed for calibration of the measuring element.

As a rule, such an ion-permeable, hydrophilic polymer layer, e.g., a hydrogel layer, is already incorporated in most state-of-the art optical pH meters. It would also be possible, however, to add it later on.

The latter also applies to electrochemical measuring elements. In such instances care must be taken, however, that the hydrogel layer covers the reference element as well.

A driftfree pH measuring element is conveniently conditioned with an aqueous solution before the actual measuring process. The chemical composition of this aqueous storage and conditioning solution is chosen such that a pH value suitable for calibration of the pH measuring element is obtained by tonometry with a gas which contains at least one component (e.g., $CO_2$) reacting acid or basic in aqueous solution.

If the conditioning and storage solution is replaced during the calibrating process by a calibrating gas with known concentration of a gas component (e.g., $CO_2$) reacting acid or basic in aqueous solution, such that residues of the conditioning solution remain in the hydrogel layer of the measuring element, the acid or basic reacting gas component will yield a pH value in the hydrogel layer of the measuring element corresponding to its gas partial pressure and the chemical composition of the residues of the conditioning solution.

The advantages of gaseous calibrating media over liquid calibrating media are obvious:

(1) Low volume and shipping weight due to storage and delivery of the compressed gaseous calibrating medium in light metal containers.

(2) Precise and easy preparation of the calibrating media by gravimetric weighing-in of the individual gaseous components.

(3) No degradation due to microbial attack, hence no need for biocides.

(4) Resistant to temperature changes under normal atmospheric conditions.

(5) No disposal after use in the instance of non-toxic gas components (no waste).

(6) No contamination due to chemical components of the storage container.

(7) No active delivery into the measuring device.

(8) No potential danger in case of leakage (in the instance of non-toxic gaseous components).

It is further proposed by the invention that the aqueous solution contain stable organic or inorganic compounds with weak acid or basic reaction as buffer components, which will lead to a predefined pH value in the hydrophilic polymer layer by reacting with the acid or basic components of the gaseous calibrating medium.

Suitable buffer components of the liquid storage and conditioning medium are components which will yield known pH values when they are in aqueous solution and in thermodynamic equilibrium with a gaseous component of a calibrating gas of known composition, which is acid or basic in aqueous solution. Type and concentration of the buffer components will depend on the pH value to be obtained and the kind of gas measuring element used for the gas component reacting acid or basic in aqueous solution.

Preferred buffer components are inorganic and organic compounds reacting acid or basic in aqueous environment, as well as their salts, such as carbonates, phosphates, phthalates, borates, tartrates, citrates, amines, bis(2-hydroxyethyl)amino-tris(hydroxymethyl)-methane (BIS-TRIS), tris (hydroxymethyl) amino-methane (TRIS), N-tris (hydroxymethyl)-methyl-2-aminoethane sulfonic acid (TES), 4-(2-hydroxyethyl)-piperazine-1-ethane sulfonic acid (HEPES), 3-morpholinopropane sulfonic acid (MOPS).

As pH values measured by means of optical pH measuring elements are strongly dependent on the ionic strength of the sample, it is considered particularly advantageous if neutral salts, preferably NaCl, KCl, or LiCl, are added to the aqueous solution in order to match the ionic strength of the solution with that of the sample to be measured.

If at least one gas measuring element is to be calibrated simultaneously with the pH measuring element, using the calibrating gas provided for the latter, the proposal is put forward that the gaseous calibrating medium contain the respective gas component of the particular gas measuring element at a concentration corresponding to the normal range of the gas partial pressure prevailing in the particular test arrangement.

According to the invention, the gaseous component $CO_2$ of the gaseous calibrating medium, which is acid in aqueous solution, can be employed for simultaneously calibrating any $CO_2$-measuring element provided in the measuring device.

For simultaneous calibration of any $O_2$ measuring element that may be provided in the measuring device, the gaseous calibrating medium must additionally contain $O_2$ at a known concentration.

For simultaneous calibration of all three measuring elements (pH, $CO_2$, $O_2$) suitable calibrating gases are composed as following:

Calibrating gas 1: 5.5% vol $CO_2$ 12.5% vol $O_2$ plus inert gas ($N_2$)

Calibrating gas 2: 11.0% vol $CO_2$ 20.1% vol $O_2$ plus inert gas ($N_2$)

After moistening, for example by contact with the storage and conditioning solution remaining at the wall of the sample channel of the measuring device, at 37° C. and an overall gas pressure of 720 torr, the above calibrating gases have the following gas partial pressures:

Calibrating gas 1: 37 torr $CO_2$ 84 torr $O_2$

Calibrating gas 2: 75 torr $CO_2$ 135 torr $O_2$

If $HCO_3^-$ are added to the storage and conditioning solution at a concentration of 18 mmole/l, following pH values are obtained in the hydrogel layer of the pH measuring element on contact with the above calibrating gases:

Calibrating gas 1: pH=7.43

Calibrating gas 2: pH=7.13

To increase wettability of the parts of the measuring device coming into contact with the sample, the addition of ionic or nonionic detergents, such as Triton-X-100 (Du Pont Company, Boston, Mass. 02118), Dehydran 241 or Dehydrol 100 (Henkel Corp., Ambier, Pa. 19002), to the aqueous solution is particularly advantageous.

The growth of bacteria or fungus often causes a change in the composition of an aqueous storage solution, in particular, its buffer components. Due to these biological activities the pH value is no longer known with sufficient accuracy for the calibrating process. It has therefore proved an advantage to add biocides to the aqueous solution, for example, NAN3, Mergal K9N (Hoechst Austria AG, A-1121 Vienna, Austria), Proclin 300 (Supelco, Inc., Supelco Park, Bellefonte, Pa. 16823), Bronidox L (Henkel Corporation, Hoboken, N.J. 07030), or Nuosept C (Huls America, Inc., Priscataway, N.J. 08855).

DESCRIPTION OF THE DRAWINGS

Following is a more detailed description of the invention as illustrated by the accompanying schematical drawings of measuring devices for implementing the method of the invention, in which FIG. 1 shows a measuring device with three measuring elements in contact with an aqueous solution, i.e., a storage solution, FIG. 2 is a section along line II—II in FIG. 1, FIGS. 3 and 4 show the measuring element of FIG. 1 and 2 in contact with the calibrating medium, FIGS. 5 and 6 show a further variant of the invention.

DETAILED DESCRIPTION OF THE PREFERRED EMBODIMENTS

Figure 7:
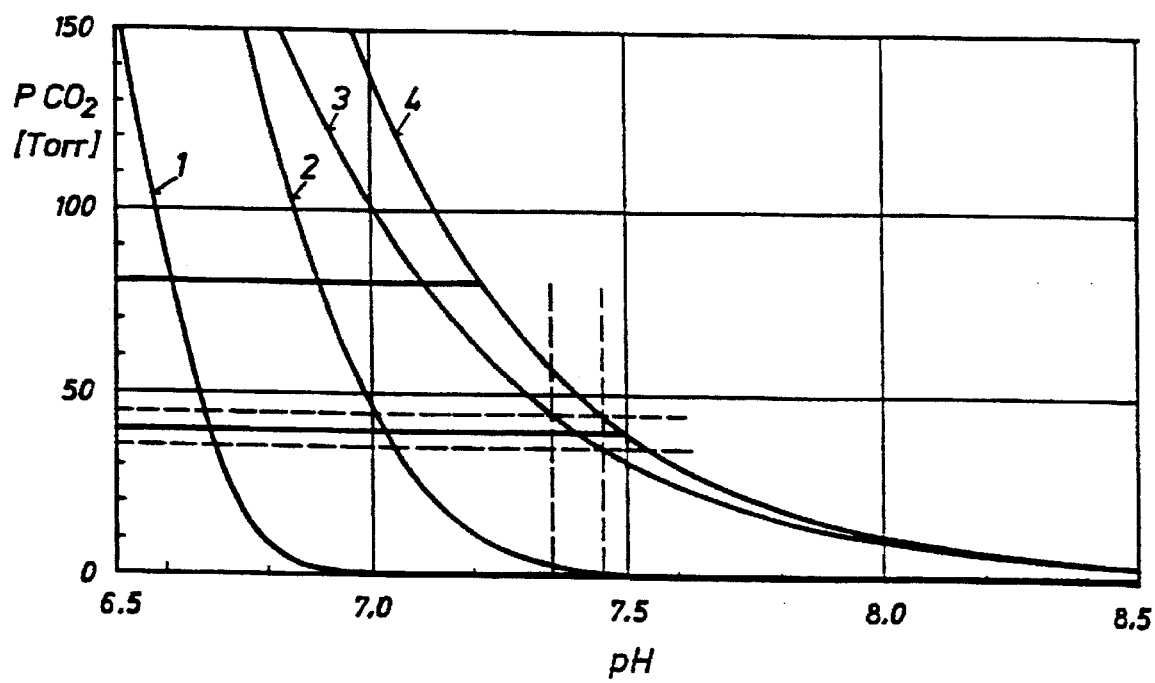
FIG. 7 is a diagram presenting pH in dependence on $CO_2$ partial pressure, for several aqueous solutions.

As is seen in FIGS. 1 to 4, at least one channel 2 and one pH measuring element 3 are arranged in a measuring device 1. The device may contain any number of gas measuring elements 4, 5. An ion-permeable layer 6 of the pH measuring element 3 is in direct contact with an aqueous solution, i.e., a storage solution 7, which is contained in the channel 2 of the arrangement. Due to this contact, the storage solution together with its chemical components penetrates the hydrogel layer of the pH measuring element. For calibration the liquid conditioning medium is replaced by a calibrating gas 8 (FIGS. 3 and 4). Residues of the storage solution 7 will remain in the ion-permeable layer 6 of the pH measuring element. By means of at least one component of the calibrating gas, which is acid or basic in aqueous solution and which reacts with the remaining storage solution in the ion-permeable layer 6 of the pH measuring element, a pH value is established which is employed for calibration of the pH measuring element. If one or several gas measuring elements are provided, the gas partial pressures of suitable gas components of the gaseous calibrating medium are employed for calibration of the gas measuring element(s).

As is seen in FIGS. 5 and 6, a single pH measuring element 3 or a pH measuring element 3 in close proximity to an optional number of gas measuring elements 4, 5 at the tip of an optical waveguide 9, may be dipped into an aqueous storage or conditioning solution 7 contained in a suitable vessel 10. For calibration the storage solution 7 is replaced by a calibrating gas 8 (see FIG. 6), or the waveguide 9 is introduced into a second vessel containing the calibrating gas.

Optical measuring elements have been described which lend themselves to simultaneous measurement of pH and at least one gaseous component (cf. O. S. WOLFBEIS, "Fiber Optic Chemical Sensors and Biosensors, vol. 2, CRC Press, Boca Raton, 1991). The method of calibration proposed in the present invention is especially well suited for use with such measuring elements.

Curve 1 in FIG. 7 shows the pH values of a common calibrating solution (0.025 mole/l $KH_2PO_4$ and $Na_2HPO_4$) at 37° C. in equilibrium with $CO_2$ containing gases with different $CO_2$ partial pressures.

Curve 2 shows the pH values of another known calibrating solution (0.0087 mole/l $KH_2PO_4$ and 0.0304 mole/l $Na_2HPO_4$) at 37° C. in equilibrium with $CO_2$ containing gases with different $CO_2$ partial pressures.

Curves 1 and 2 show that phosphate buffers (pH 7.38) which are frequently used for calibration of a pH measuring element, are not suitable for simultaneous calibration of a pH and a $CO_2$ measuring element in the physiologically normal range of blood (pH 7.35–7.45, $PCO_2$ 35–45 torr), since in equilibrium with 40 torr $CO_2$ no adequate pH value will result in this range.

Curve 3 shows pH behavior according to the invention, using a contact solution containing 0.018 mole/l $NaHCO_2$. At 37° C. and in equilibrium with 40 torr $CO_2$ the solution has a pH of 7.39. The curve also indicates that an often needed second calibrating point may be obtained with this solution. For example, at 37° C. and in equilibrium with 80 torr $CO_2$, a pH of 7.09 is established.

Curve 4 shows pH behavior if a further contact solution is used, consisting of different buffer components and a neutral salt for adjusting ionic strength. (Composition: 0.022 mole/l $HCO_3^-$, 0.013 mole/l $HPO_4^-$, 0.1 mole/l NaCl). By using several different buffer components the pH values of the solution can be precisely adjusted in dependence on $CO_2$ partial pressure.

I claim:

1. A method for calibration of a pH measuring element which includes an ion-permable, hydrophilic polymer layer, said method comprising the steps of:
   a) contacting said polymer layer with an aqueous solution prior to calibration, said aqueous solution containing stable organic or inorganic compounds as weak acid or basic reacting buffer components;
   b) displacing or replacing said aqueous solution by a gaseous calibrating medium, residues of said aqueous solution remaining in said ion-permeable, hydrophilic polymer layer, and wherein said gaseous calibrating medium contains a known amount of at least one component which reacts acid or basic in aqueous solution;
   c) enabling reaction of said at least one acid or basic component of said gaseous calibrating medium with said buffer components of said remaining residues of said aqueous solution in said polymer layer, such that a defined pH value is established in said polymer layer; and
   d) employing said defined pH value of step c) for calibration of said pH measuring element.

2. A method according to claim 1, wherein said buffer components are inorganic and organic compounds reacting acid or basic in aqueous environment, as well as their salts selected from the group consisting of carbonates, phosphates, phthalates, borates, tartrates, citrates, amines, bis(2-hydroxyethyl)amino-tris (hydroxymethyl)-methane (BIS-TRIS), tris(hydroxymethyl), amino-methane (TRIS), N-tris (hydroxymethyl)-methyl-2-aminoethane sulfonic acid (TES), 4-(2-hydroxyethyl)-piperazine-1-ethane sulfonic acid (HEPES) and 3-morpholinopropane sulfonic acid (MOPS).

3. A method according to claim 2, including adding a neutral salt to said aqueous solution of step a) in order to match the ionic strength of said aqueous solution with the ionic strength of a sample to be measured with said pH measuring element.

4. A method according to claim 3, wherein said neutral salt is selected from the group consisting of NaCl, KCl, and LiCl.

5. A method according to claim 1, including adding a neutral salt to said aqueous solution of step a) in order to match the ionic strength of said aqueous solution with the ionic strength of a sample to be measured with said pH measuring element.

6. A method according to claim 1, wherein ionic or nonionic detergents are added to said aqueous solution in step a).

7. A method according to claim 1, wherein biocides from a group consisting of $NaN_3$, Mergal K9N, Proclin 300, Bronidox L, and Nuosept C are added to the aqueous solution in step a).

8. A method for calibration of a pH measuring element which includes an ion-permeable, hydrophilic polymer layer and for simultaneously calibrating at least one gas measuring element from the group consisting of $CO_2$, $O_2$, $SO_2$, $NH_3$, and $H_2S$ measuring elements, comprising the steps of:
   a) contacting said polymer layer with an aqueous solution prior to calibration, said aqueous solution containing stable organic or inorganic compounds as weak acid or basic reacting buffer components;
   b) displacing or replacing said aqueous solution by a gaseous calibrating medium, residues of said aqueous solution remaining in said ion-permeable, hydrophilic polymer layer, and wherein said gaseous calibrating medium contains a known amount of at least one component which reacts acid or basic in aqueous solution and further contains the at least one gas component for calibration of said at least one gas measuring element at a concentration corresponding to a normal range of the gas partial pressure of a sample to be measured with said gas measuring element;
   c) enabling reaction of said at least one acid or basic component of said gaseous calibrating medium with said buffer components of said remaining residues of said aqueous solution in said polymer layer, such that a defined pH value is established in said polymer layer;
   d) employing said defined pH value of step c) for calibration of said pH measuring element; and
   e) calibrating said at least one gas measuring element with said at least one gas component.

9. A method according to claim 8, wherein said buffer components are inorganic and organic compounds reacting acid or basic in aqueous environment, as well as their salts of a group consisting of carbonates, phosphates, phthalates, borates tartrates, citrates, amines, bis(2-hydroxyethyl) amino-tris (hydorxymethyl) amino-methane (TRIS), N-tris (hydroxymethyl)-methyl-2-aminoethane sulfonic acid (TES), 4-(2-hydroxyethyl)-piperazine-1-ethane sulfonic acid (HEPES) and 3-morpholinopropane sulfonic acid (MOPS).

10. A method according to claim 8, including adding a neutral salt to said aqueous solution of step a) in order to match the ionic strength of said aqueous solution with the ionic strength of a sample to be measured with said measuring element.

11. A method according to claim 8, wherein a given $CO_2$ partial pressure in said gaseous calibrating medium of step b) is used both as said gas component for calibrating said $CO_2$ measuring element in step e) and as said acid reacting component for calibration of said pH measuring element in step d).

12. A method according to claim 8, wherein $O_2$ is used as additional gaseous component in step b) for calibrating said $O_2$ measuring element in step d).

13. A method according to claim 8, wherein ionic or nonionic detergents are added to said aqueous solution in step a).

14. A method according to claim 8, wherein biocides from a group consisting of $NAN_3$, Mergal K9N, Proclin 300, Bronidox L, and Nuosept C are added to the aqueous solution in step a).

* * * * *